(12) United States Patent
Shields et al.

(10) Patent No.: US 10,022,252 B2
(45) Date of Patent: Jul. 17, 2018

(54) SPIRAL BLOOD FLOW DEVICE WITH DIAMETER INDEPENDENT HELIX ANGLE

(71) Applicant: Cook Medical Technologies LLC, Bloomington, IN (US)

(72) Inventors: Adam Shields, Lafayette, IN (US); Keith Milner, West Lafayette, IN (US); Melissa Lonn, Lafayette, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 64 days.

(21) Appl. No.: 15/012,274

(22) Filed: Feb. 1, 2016

(65) Prior Publication Data

US 2016/0361181 A1 Dec. 15, 2016

Related U.S. Application Data

(60) Provisional application No. 62/175,754, filed on Jun. 15, 2015, provisional application No. 62/173,639, filed on Jun. 10, 2015.

(51) Int. Cl.
| | |
|---|---|
| *A61F 2/82* | (2013.01) |
| *A61F 2/90* | (2013.01) |
| *A61F 2/06* | (2013.01) |
| *A61F 2/86* | (2013.01) |
| *A61F 2/89* | (2013.01) |
| *A61F 2/844* | (2013.01) |

(Continued)

(52) U.S. Cl.
CPC ............... *A61F 2/90* (2013.01); *A61F 2/06* (2013.01); *A61F 2/844* (2013.01); *A61F 2/86* (2013.01); *A61F 2/89* (2013.01); *A61F 2/82* (2013.01); *A61F 2/915* (2013.01); *A61F 2/962* (2013.01); *A61F 2002/068* (2013.01); *A61F 2002/825* (2013.01); *A61F 2002/9155* (2013.01); *A61F 2210/0014* (2013.01); *A61F 2250/0058* (2013.01)

(58) Field of Classification Search
CPC .................................................. A61F 2002/825
See application file for complete search history.

(56) References Cited

U.S. PATENT DOCUMENTS

| | | | |
|---|---|---|---|
| 5,344,425 | A | 9/1994 | Sawyer |
| 6,616,675 | B1 | 9/2003 | Evard et al. |
| 6,776,194 | B2 | 8/2004 | Houston et al. |

(Continued)

FOREIGN PATENT DOCUMENTS

| | | |
|---|---|---|
| DE | 102007015462 A1 | 10/2008 |
| EP | 2136734 | 12/2013 |

(Continued)

*Primary Examiner* — Yashita Sharma
*Assistant Examiner* — Rebecca Preston
(74) *Attorney, Agent, or Firm* — Liell + McNeil

(57) ABSTRACT

A spiral blood flow device includes a stent made up of a plurality of expansion members joined to a plurality of axial members that permit the stent to change diameter among a continuum of expanded configurations. The axial members have fixed orientation, whereas the expansion members have a variable orientation relative to the longitudinal axis throughout the continuum of expanded configurations. A spiral flow inducing structure, which may include fins attached to the axial members, define a helical flow angle that remains constant throughout the continuum of expanded configurations.

20 Claims, 2 Drawing Sheets

(51) Int. Cl.
*A61F 2/962* (2013.01)
*A61F 2/915* (2013.01)

(56) References Cited

U.S. PATENT DOCUMENTS

| | | | |
|---|---|---|---|
| 7,128,750 B1 | 10/2006 | Stergiopulos | |
| 7,331,989 B2 | 2/2008 | Houston et al. | |
| 7,682,673 B2 | 3/2010 | Houston et al. | |
| 8,382,697 B2 | 2/2013 | Brenneman et al. | |
| 8,523,800 B2 | 9/2013 | Brenneman et al. | |
| 8,811,267 B2 | 8/2014 | Kim et al. | |
| 2004/0037986 A1* | 2/2004 | Houston | A61F 2/06 428/36.9 |
| 2007/0191927 A1 | 8/2007 | Bowe et al. | |
| 2007/0204445 A1* | 9/2007 | Hood | A61F 2/06 28/143 |
| 2007/0270939 A1* | 11/2007 | Hood | A61F 2/82 623/1.22 |
| 2008/0140110 A1* | 6/2008 | Spence | A61F 2/06 606/200 |
| 2011/0093002 A1* | 4/2011 | Rucker | A61F 2/90 606/198 |
| 2011/0190871 A1* | 8/2011 | Trollsas | A61F 2/91 623/1.15 |
| 2012/0130314 A1* | 5/2012 | Stonebridge | A61F 2/88 604/175 |
| 2013/0331927 A1* | 12/2013 | Zheng | A61F 2/82 623/1.19 |
| 2014/0031920 A1* | 1/2014 | Malek | A61F 2/86 623/1.16 |

FOREIGN PATENT DOCUMENTS

| | | |
|---|---|---|
| WO | 9844869 | 10/1998 |
| WO | 00/38591 | 7/2000 |
| WO | 2004/014474 A1 | 2/2004 |

\* cited by examiner

SPIRAL BLOOD FLOW DEVICE WITH DIAMETER INDEPENDENT HELIX ANGLE

TECHNICAL FIELD

The present disclosure relates generally to stents that include spiral flow inducing structures, and more particularly to a spiral flow inducing structure with a helix angle that is independent of the diameter of the stent.

BACKGROUND

Due in part to the lack of transplant availability, many patients with end-stage renal disease receive regular hemodialysis treatments. To minimize treatment time, hemodialysis requires a large blood volume flow rate that is typically achieved through the surgical creation of an arteriovenous shunt. This creates a low resistance pathway that results in significantly increased flow rates through a graft or an arteriovenous fistula (AVF). After surgical creation of an AVF, the inflow and outflow vessels must dilate sufficiently, and the venous tissue must undergo a remodeling process known as "fistula maturation" in order to be able to sustain the high flow rates necessary for hemodialysis. One common problem with AVFs is tissue proliferation along the lumen of the vein known as neointimal hyperplasia (NIH), which can lead to stenosis, reduced flow, and ultimately failure of the fistula. The progression of NIH may be, in part, the venous tissue's response to the abnormal hemodynamic stresses which result from the increased flow rates and large pressure drop across an arteriovenous anastomosis. The abnormal flow through an AVF appears to be generally turbulent rather than laminar.

Several reports suggest that the native state of arterial blood flow may exhibit circumferentially oriented velocity components such that the blood flow is helical or spiral in nature. The spiral blood flow is thought to play a roll in maintaining healthy vascular function. Thus, it may be possible that creating spiral blood flow in the vicinity of an AVF could help prevent or slow the progression of NIH.

One aspect of fistula maturation is significant venous dilation up to roughly 150% of the vein's original diameter. While there are several devices known for inducing spiral blood flow, some of them have fixed diameters rendering them unsuitable to accommodate vessel diameter changes due to fistula maturation. Other spiral flow devices that can accommodate a variable diameter typically include a spiral blood flow inducing structure that changes in its helix angle geometry with changes in the diameter of the device. One example in this regard is taught in U.S. Pat. No. 7,682,673. This change in the spiral inducing properties of the device may be undesirable, and may cause the device to diverge away from some desired helix angle.

The present disclosure is directed toward one or more of the problems set forth above.

SUMMARY

In one aspect, a spiral blood flow device includes a stent having a longitudinal axis and being movable among a transport configuration and a continuum of expanded configurations. The stent includes a plurality of expansion members joined to a plurality of axial members. Each of the axial members has a fixed orientation relative to the longitudinal axis throughout the continuum of expanded configurations, while the expansion members each have a variable orientation relative to the longitudinal axis throughout the continuum of expanded configurations. A spiral flow inducing structure is attached to each of the plurality of axial members to define a helical flow angle relative to the longitudinal axis. The helical flow angle is constant throughout the continuum of expanded configurations.

In another aspect, a method of impeding neointimal hyperplasia includes moving a spiral blood flow device in a transport configuration to an implantation site. The spiral blood flow device is implanted at the implantation site at least in part by expanding the stent to a first diameter in a continuum of expanded configurations. Spiral flow is induced in blood flowing through the spiral blood flow device with a spiral flow inducing structure. The spiral blood flow device is changed from the first diameter to a second diameter in the continuum of expanded configurations responsive to a vessel diameter increase at the implantation site. The helical flow angle is maintained constant throughout the change from the first diameter to the second diameter.

DETAILED DESCRIPTION

Figure 1:
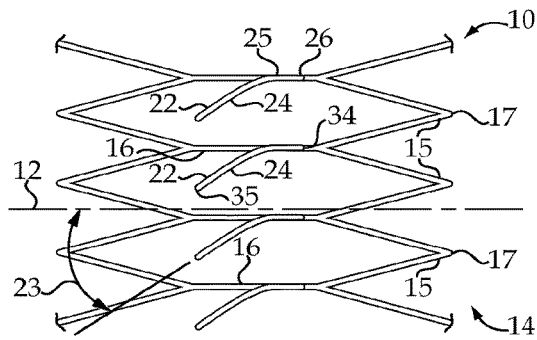
FIG. 1 is an unrolled schematic view of a spiral blood flow device according to the present disclosure.
Figure 2:
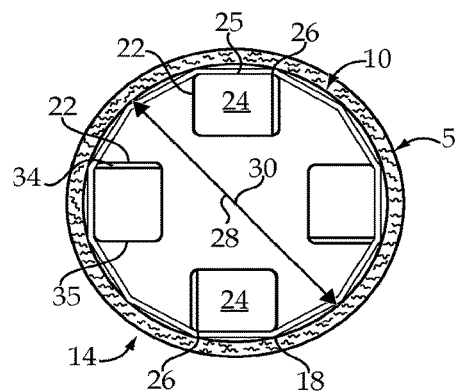
FIG. 2 is an end view of the spiral blood flow device of FIG. 1 implanted in a vessel.
Figure 3:
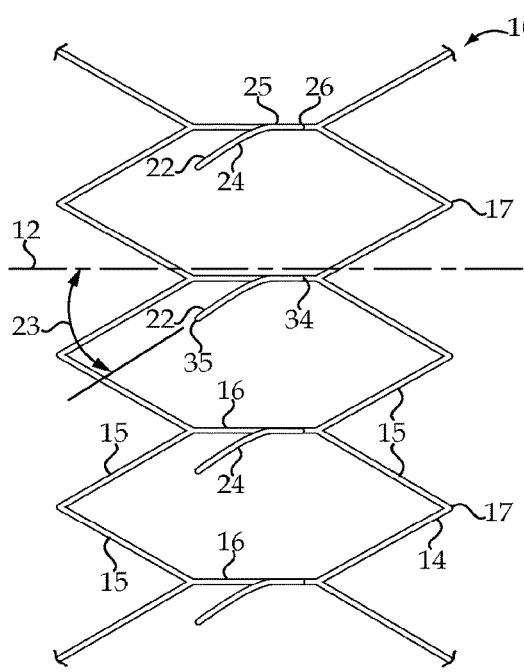
FIG. 3 is an unrolled schematic view of the spiral blood flow device of FIG. 1 after the vessel diameter has enlarged.
Figure 4:
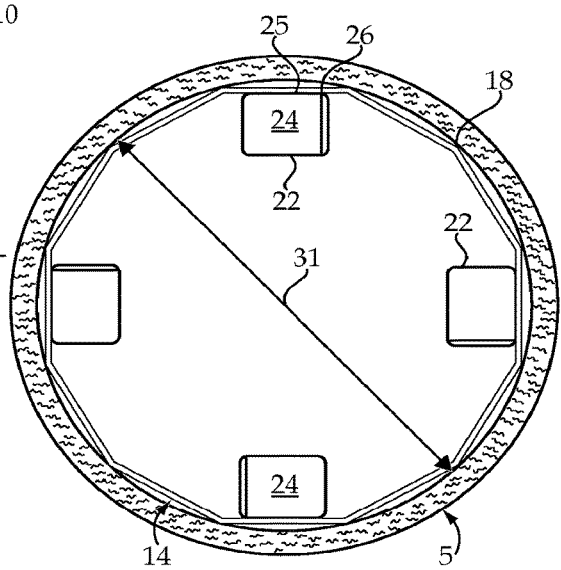
FIG. 4 is an end view of the spiral blood flow device of FIG. 3 after the vessel of FIG. 2 has enlarged.

Referring initially to FIGS. 1-4, a spiral blood flow device 10 is shown in 2 different expanded configurations 14 of a continuum of expanded configurations. FIGS. 1 and 3 show the spiral blood flow device 10 schematically unrolled, whereas FIGS. 2 and 4 show spiral blood flow device 10 implanted in a vessel 5. Spiral blood flow device 10 includes a stent 11 having a longitudinal axis 12, and being movable among a transport configuration 13 (FIG. 5) and a continuum of expanded configurations 14. Stent 11 includes a plurality of expansion members 15 joined to a plurality of axial members 16. Each of the axial members 16 has a fixed orientation relative to the longitudinal axis 12 throughout the continuum of expanded configurations 14. The expansion members 15 each have a variable orientation relative to the longitudinal axis 12 throughout the continuum of expanded configurations 14. Those skilled in the art will appreciate that stent 11 can be either a self expanding stent or a balloon expanded stent, and may be manufactured in a variety of different ways from different materials including but not limited to being cannula cut, sheet cut, and/or formed spring wire. The materials include but are not limited to nitinol, stainless steel and maybe plastics or composites, which may be uncoated or coated with a suitable material known in the art.

A spiral flow inducing structure 22 is attached to each of the plurality of axial members 16 to define a helical flow angle 23 relative to the longitudinal axis 12. The helical flow angle 23 is constant throughout the continuum of expanded configurations 14. In the illustrated embodiment, this is accomplished by utilizing a spiral flow inducing structure 22 in the form of fins 24 attached at one edge 25 to a respective one of the plurality of axial members 16. The helical flow angle 23 may be predetermined at time of manufacture, but the fins 24 may be compressible so that the spiral blood flow device 10 can be compressed into a transport configuration 13. Upon release, the fins 24 may resiliently assume their predetermined shape and orientation using techniques known in the art, such as by heat treating and setting the shape in the event that spiral blood flow device 10 were made from nitinol. In the illustrated embodiment, all of the fins 24 are identically shaped. Nevertheless, a spiral blood flow device 10 having two or more different shaped fins or other structures constituting the spiral flow inducing structure 22 would also fall within the intended scoped of the present disclosure. Although the illustrated embodiment shows four fins 24, any number of fins from one to four or more would also fall within the intended scoped of the present disclosure. In a further effort to insure that the helical flow angle 23 remains constant throughout the continuum of expanded configurations 14, each of the fins 24 may be attached at exactly one attachment 26 to the respective one of the plurality of axial members 16, as shown. In the illustrated embodiment, the helical flow angle 23 is defined by a tangent to the fin 24 at the trailing edge 35. Nevertheless, the helical flow angle according to the present disclosure could be defined in other ways, including but not limited to drawing a straight line through the leading edge 34 and the trailing edge 35. In any event, however the helical flow angle 23 is defined in a specific case, it remains constant throughout the continuum of expanded configurations according to the present disclosure.

Figure 5:
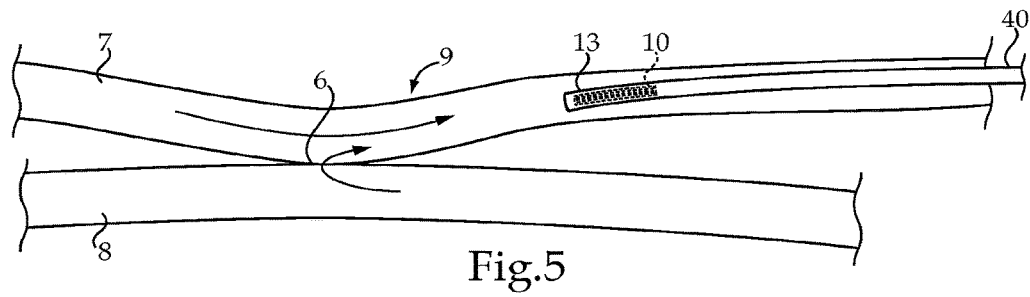
FIG. 5 is a side view of an AVF while a spiral blood flow device of the present disclosure is being maneuvered to an implantation site.
Figure 6:
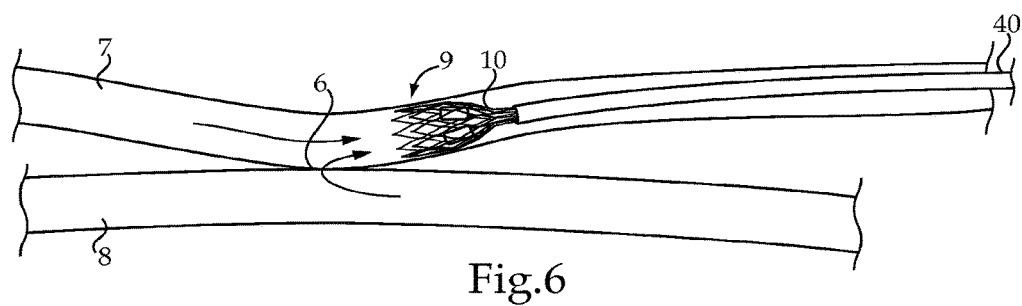
FIG. 6 is a view similar to view 5 except showing a spiral blood flow device being implanted at the implantation site.

In the illustrated embodiment, the plurality of axial members 16 are oriented parallel to the longitudinal axis 12 throughout the continuum of expanded configurations. Nevertheless, the axial members could have other orientations, such as perpendicular to the longitudinal axis 12, without departing from the intended scope of the present disclosure. Although not necessary, the plurality of axial members 16 may also be oriented parallel to the longitudinal axis 12 in the transport configuration 13, such as when the spiral blood flow device 10 is compressed in a delivery catheter 40 as shown in FIG. 5. In the illustrated embodiment, the plurality of axial members 16 are attached at opposite ends to vertices 17 that change shape throughout the continuum of expanded configurations 14. Nevertheless, those skilled in the art will appreciate that a wide variety of different stent structures with struts having a variety of different orientations could also fall within the intended scope of the present disclosure. Like most stents, both the expansion members 15 and the axial members 16 may include a vessel contact surface 18 that is radially remote from longitudinal axis 12 in a manner well known in the art. The illustrated embodiment shows a self expanding stent, but a suitable balloon expanded stent could also fall within the scope of the present disclosure.

INDUSTRIAL APPLICABILITY

The present disclosure finds general applicability to devices for inducing spiral blood flow in a vessel. The present disclosure finds specific applicability to implantation in the vicinity of an a arteriovenous fistula (AVF) in order to undermine or inhibit neointimal hyperplasia.

Figure 7:
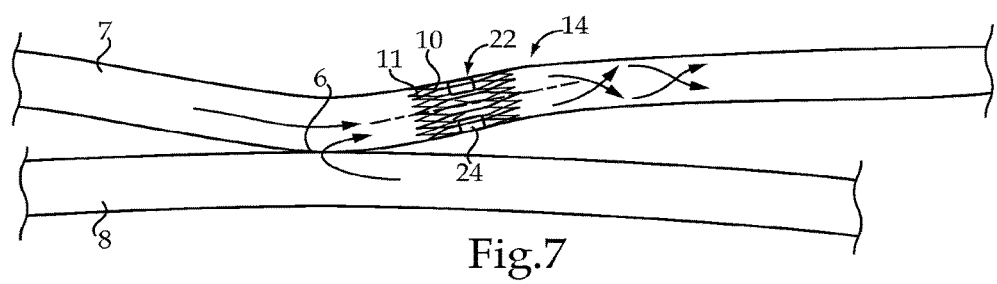
FIG. 7 is a view similar to FIG. 6 after implantation of the spiral blood flow device and showing spiral flow being induced in blood flow through the device.
Figure 8:
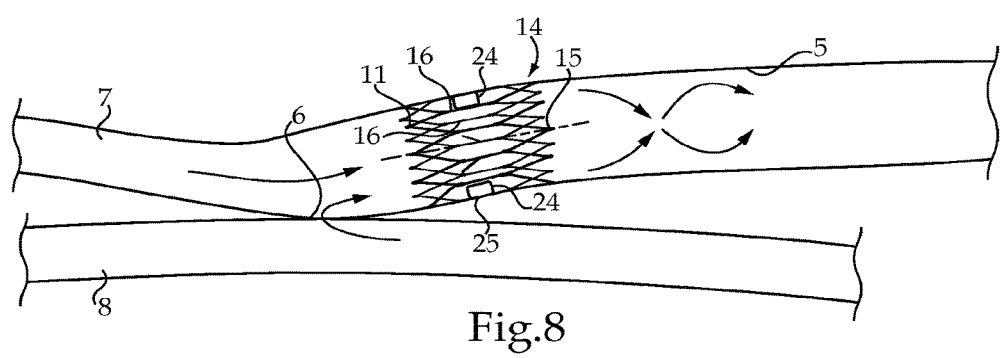
FIG. 8 is a view similar to FIG. 7 except showing the vessel at the implantation site expanded to a larger diameter but still inducing spiral blood flow at a helix angle that is the same of that of FIG. 7.

Referring now in addition to FIGS. 5-9, a method of impeding neointimal hyperplasia with a spiral blood flow device 10 includes moving the spiral blood flow device 10 in a transport configuration 13 to an implantation site 9. For instance, a spiral blood flow device 10 may be compressed and carried to implantation site 9 using a suitable delivery catheter 40 in a manner well known in the art with regard to the delivery of self expanding stents. After arrival at implantation site 9, the spiral blood flow device 10 is implanted at the implantation site 9 at least in part by expanding the stent to a first diameter 30 (FIG. 2) in the continuum of expanded configurations 14. During the implantation, one could expect the various fins 24 to resiliently unfold or unfurl from a compressed state to the shape and orientation shown. In the illustrated embodiment, each of the fins 24 may have a leading edge 34 oriented parallel to longitudinal axis 12 and then the surface of the fin 24 turns the fluid through helical flow angle 23 so that the tangent to trailing edge 35 is oriented at the helical flow angle 23. After the fins 24 unfurl, the spiral blood flow inducing structure 22 induces spiral flow in blood flowing through device 10, as best shown by the arrows in FIGS. 7 and 8. Although not necessary, spiral blood flow device 10 is shown being implanted in the vicinity of an AVF 6 that fluidly joins an artery 8 to a vein 7 in a manner well known in the art. As the AVF matures, the vessel 5 may tend to increase in diameter, such as grow from a first diameter 30, as shown in FIGS. 2 and 7 to a second diameter 31 as shown in FIGS. 4 and 8. When this occurs, the helical flow angle 23 defined by the fins 24 in particular and the spiral flow inducing structure 22 in general remains constant throughout the change from the first diameter 30 to the second diameter 31.

In the case of a self expanding stent 11, the implantation may be accomplished using known techniques by releasing the spiral blood flow device 10 to self expand at the implantation site 9. However, in the event that the stent 11 is a balloon expanded stent, the implantation might include inflating a balloon to facilitate implantation at the implantation site 9 in a manner well known in the art. During implantation, one could expect the plurality of axial members 16 and the plurality of expansion members 15 to move into contact with the wall of vessel 5 at contact surfaces 18. When this occurs, the fins 24 of the spiral blood flow device may deploy from a previously furled or compressed configuration into the spiral flow inducing structure that defines the constant helical flow angle 23 as best shown in FIGS. 1 and 3. In the event that the spiral flow inducing device 10 is delivered to an implantation site 9 in proximity to an AVF 6, one could expect the diameter 28 of the self expanding stent 11 to range from between two millimeters to six millimeters over the continuum of expanded configurations 14. Nevertheless, one could expect in a typical application for the diameter of the vessel 5 to dilate up to roughly 150% of the original diameter 30 up to the enlarged diameter 31.

As the understanding of spiral blood flow and preferred helical flow angles matures, the spiral blood flow device 10 of the present disclosure can be utilized to pre-set the helical flow angle 23 of the device prior to implantation and be assured that that desired helical flow angle 23 remains constant throughout the maturation of the AVF, with one of the intended purposes being to inhibit or impede neointimal plasia in particular and to increase the success rate of AVFs in general.

It should be understood that the above description is intended for illustrative purposes only, and is not intended to limit the scope of the present disclosure in any way. Thus, those skilled in the art will appreciate that other aspects of the disclosure can be obtained from a study of the drawings, the disclosure and the appended claims.

What is claimed is:

1. A spiral blood flow device comprising:
   a stent having a longitudinal axis and being movable among a transport configuration and a continuum of expanded configurations;
   the stent including a plurality of expansion members joined to a plurality of axial members, and wherein each of the axial members have a fixed orientation relative to the longitudinal axis throughout the continuum of expanded configurations, and the expansion members each have a variable orientation relative to the longitudinal axis throughout the continuum of expanded configurations;
   a spiral flow inducing structure attached to each of the plurality of axial members defining a helical flow angle relative to the longitudinal axis; and
   the helical flow angle being a constant throughout the continuum of expanded configurations.

2. The spiral blood flow device of claim 1 wherein each of the spiral flow inducing structures includes a fin attached at one edge to a respective one of the plurality of axial members.

3. The spiral blood flow device of claim 2 wherein each of the fins is identically shaped.

4. The spiral blood flow device of claim 3 wherein each of the fins is attached at exactly one attachment to the respective one of the plurality of axial members.

5. The spiral blood flow device of claim 1 wherein each of the plurality of axial members is oriented parallel to the longitudinal axis throughout the continuum of expanded configurations.

6. The spiral blood flow device of claim 5 wherein each of the plurality of axial members is oriented parallel to the longitudinal axis in the transport configuration.

7. The spiral blood flow device of claim 6 wherein each of the spiral flow inducing structures includes a fin attached at one edge to a respective one of the plurality of axial members.

8. The spiral blood flow device of claim 7 wherein each of the fins is identically shaped.

9. The spiral blood flow device of claim 1 wherein each of the plurality of axial members is attached at opposite ends to vertices that change shape throughout the continuum of expanded configurations.

10. The spiral blood flow device of claim 1 wherein each of the plurality of axial members has a vessel contact surface radially remote from the longitudinal axis.

11. The spiral blood flow device of claim 1 wherein the stent is a self expanding stent.

12. The spiral blood flow device of claim 11 wherein a diameter of the self expanding stent ranges from 2 mm to 6 mm over the continuum of expanded configurations.

13. The spiral blood flow device of claim 1 wherein each of the plurality of axial members is orientated parallel to the longitudinal axis in the transport configuration and throughout the continuum of expanded configurations;
   wherein each of the plurality of axial members is attached at opposite ends to vertices that change shape throughout the continuum of expanded configurations, and each of the plurality of axial members has a vessel contact surface radially remote from the longitudinal axis;
   wherein each of the spiral flow inducing structures includes a fin attached at one edge to a respective one of the plurality of axial members, and each of the fins is identically shaped; and
   wherein the stent is a self expanding stent.

14. A method of impeding neointimal hyperplasia with a spiral blood flow device that includes a stent having a longitudinal axis and being movable among a transport configuration and a continuum of expanded configurations; the stent including a plurality of expansion members joined to a plurality of axial members, and wherein each of the axial members have a fixed orientation relative to the longitudinal axis throughout the continuum of expanded configurations, and the expansion members each have a variable orientation relative to the longitudinal axis throughout the continuum of expanded configurations; a spiral flow inducing structure attached to each of the plurality of axial members defining a helical flow angle relative to the longitudinal axis; and the helical flow angle being a constant throughout the continuum of expanded configurations, and the method comprising the steps of:
   moving the spiral blood flow device in the transport configuration to an implantation site;
   implanting the spiral blood flow device at the implantation site at least in part by expanding the stent to a first diameter in the continuum of expanded configurations;
   inducing spiral flow in blood flowing through the spiral blood flow device with the spiral flow inducing structure;
   changing the spiral blood flow device from the first diameter to a second diameter in the continuum of expanded configurations responsive to a vessel diameter increase at the implantation site; and
   maintaining the helical flow angle constant throughout the change from the first diameter to the second diameter.

15. The method of claim 14 wherein the implanting step includes releasing the spiral blood flow device to self expand at the implantation site.

16. The method of claim 15 wherein the implanting step includes moving the plurality of axial members of the stent into contact with a vessel wall, and deploying a plurality of fins of the spiral flow inducing structure to define the helical flow angle.

17. The method of claim 16 wherein each of the plurality of axial members is oriented parallel to the longitudinal axis throughout the change from the first diameter to the second diameter.

18. The method of claim 17 wherein each of the plurality of axial members is oriented parallel to the longitudinal axis in the transport configuration.

19. The method of claim 18 wherein each of the plurality of axial members is attached at opposite ends to vertices that change shape during the implanting step and during the change from the first diameter to the second diameter.

20. The method of claim 19 wherein the continuum of expanded configurations corresponds to a diameter of the stent ranging from 2 mm to 6 mm.

* * * * *